(12) United States Patent
Freed et al.

(10) Patent No.: US 10,083,161 B2
(45) Date of Patent: Sep. 25, 2018

(54) CRITERIA MODIFICATION TO IMPROVE ANALYSIS

(71) Applicant: International Business Machines Corporation, Armonk, NY (US)

(72) Inventors: Andrew R. Freed, Cary, NC (US); Mario J. Lorenzo, Miami, FL (US); Jeffrey B. Nowicki, Oronoco, MN (US); Daniel Z. Pierce, Rochester, MN (US); Jerry L. Von Berge, Byron, MN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 146 days.

(21) Appl. No.: 14/884,217

(22) Filed: Oct. 15, 2015

(65) Prior Publication Data

US 2017/0109333 A1   Apr. 20, 2017

(51) Int. Cl.
   *G06F 17/00* (2006.01)
   *G06F 17/24* (2006.01)
   *G06F 17/30* (2006.01)

(52) U.S. Cl.
   CPC ...... *G06F 17/241* (2013.01); *G06F 17/30684* (2013.01)

(58) Field of Classification Search
   CPC ......... G06F 17/30368; G06F 17/30227; G06F 17/30088; G06F 17/30575; G06F 17/3033;
   (Continued)

(56) References Cited

U.S. PATENT DOCUMENTS 6,778,995 B1  8/2004 Gallivan
7,003,519 B1 *  2/2006 Biettron ............ G06F 17/30713
                                                                707/711
(Continued)

FOREIGN PATENT DOCUMENTS

WO   WO 2016200667 A1 * 12/2016   ....... G06F 17/30705

OTHER PUBLICATIONS

Chapman et al., "Anaphoric reference in clinical reports: Characteristics of an annotated corpus", Journal of Biomedical Informatics, Journal Article, vol. 45, Issue 3, pp. 507-521 (15 pages), published Jun. 2012 (Jul. 9, 2012) (Downloaded May 25, 2015).

(Continued)

*Primary Examiner* — Scott Baderman
*Assistant Examiner* — Jason Edwards
(74) *Attorney, Agent, or Firm* — Patterson + Sheridan, LLP

(57) ABSTRACT

Systems, methods, and computer program products to perform an operation comprising receiving a policy document specifying a plurality of criteria, identifying, in a segment of unstructured text in the policy document, a criteria delimiter, creating a first portion and a second portion of the segment of unstructured text, wherein the first and second portions are created based on the criteria delimiter, wherein the first and second portions comprise a first criterion and a second criterion, respectively, and responsive to identifying an anaphora in the second portion of the segment of unstructured text that is related to a term in the first portion of the segment of unstructured text, combining the first criterion and the second criterion into a composite criterion.

20 Claims, 6 Drawing Sheets

(58) Field of Classification Search
CPC ............. G06F 17/30684; G06F 17/241; G06F 17/30569; G06F 17/30705; G06F 17/30598
USPC .......................................................... 715/230
See application file for complete search history.

(56) References Cited

U.S. PATENT DOCUMENTS

| | | | |
|---|---|---|---|
| 7,899,666 B2 | 3/2011 | Varone | |
| 8,595,245 B2 | 11/2013 | Cavestro et al. | |
| 9,009,029 B1 | 4/2015 | Michalak et al. | |
| 9,116,982 B1* | 8/2015 | Stern ................. | G06F 17/30707 |
| 9,672,251 B1* | 6/2017 | Whang ............. | G06F 17/30528 |
| 2009/0049034 A1* | 2/2009 | Gupta ............... | G06F 17/30734 |
| 2009/0327115 A1* | 12/2009 | Schilder ............... | G06F 17/278 705/35 |
| 2011/0113032 A1 | 5/2011 | Boscolo et al. | |
| 2012/0226974 A1* | 9/2012 | Mohan ..................... | G06N 5/02 715/256 |
| 2013/0041920 A1 | 2/2013 | Bufe et al. | |
| 2013/0262361 A1* | 10/2013 | Arroyo .................... | G06N 5/02 706/46 |
| 2013/0346066 A1 | 12/2013 | Deoras et al. | |
| 2014/0257792 A1 | 9/2014 | Gandrabur et al. | |
| 2014/0280044 A1* | 9/2014 | Huynh .............. | G06F 17/30477 707/722 |
| 2015/0081281 A1 | 3/2015 | Bustelo et al. | |
| 2015/0120738 A1 | 4/2015 | Srinivasan | |
| 2015/0309990 A1* | 10/2015 | Allen .................. | G06F 17/2785 704/9 |
| 2016/0092549 A1* | 3/2016 | Byron ............... | G06F 17/30424 707/739 |
| 2016/0154787 A1* | 6/2016 | Allen .................... | G06F 17/271 704/9 |
| 2016/0156578 A1* | 6/2016 | Allen ................ | G06F 17/30867 709/206 |
| 2016/0170949 A1* | 6/2016 | Allen .................... | G06F 17/241 715/230 |
| 2016/0299934 A1* | 10/2016 | Karandikar ....... | G06F 17/30368 |

OTHER PUBLICATIONS

Savova et al., "Anaphoric relations in the clinical narrative: corpus creation", Journal of the American Medical Informatics Association, Journal Article, vol. 18, No. 4, pp. 459-465 (7 pages), published Jul. 2011 (Jul. 11, 2011) (Downloaded May 25, 2015).

* cited by examiner

CRITERIA MODIFICATION TO IMPROVE ANALYSIS

BACKGROUND

The present disclosure relates to computer software, and more specifically, to computer software which modifies criteria in a policy document during an ingestion phase to improve subsequent runtime analysis.

Unstructured text is not always provided in an ideal form for ingestion by software applications. Policy documents (such as insurance policies, clinical trial/study documents, and the like) contain individual criteria that must be ingested, evaluated, and scored before the applications can later compare cases against the criteria to determine whether the case meets the criteria. However, many problems arise when ingesting unstructured text in policy documents. For example, multiple criteria that are tightly related generally should be aggregated into one criterion for processing. Similarly, a single delimited paragraph or list may contain more criteria that can be properly evaluated as an aggregate criterion, and should be split into individual criteria. However, during the ingestion process, these opportunities to combine or split the criteria are missed. This causes detrimental results to ingestion processing time, runtime processing time, and accuracy of evaluation/scoring when processing cases.

SUMMARY

Embodiments disclosed herein provide systems, methods, and computer program products to perform an operation comprising receiving a policy document specifying a plurality of criteria, identifying, in a segment of unstructured text in the policy document, a criteria delimiter, identifying a first portion and a second portion of the segment of unstructured text, wherein the first and second portions are identified based on the criteria delimiter, wherein the first and second portions comprise a first criterion and a second criterion, respectively, and responsive to identifying an anaphora in the second portion of the segment of unstructured text that is related to a term in the first portion of the segment of unstructured text, combining the first criterion and the second criterion into a composite criterion.

DETAILED DESCRIPTION

Figure 1:
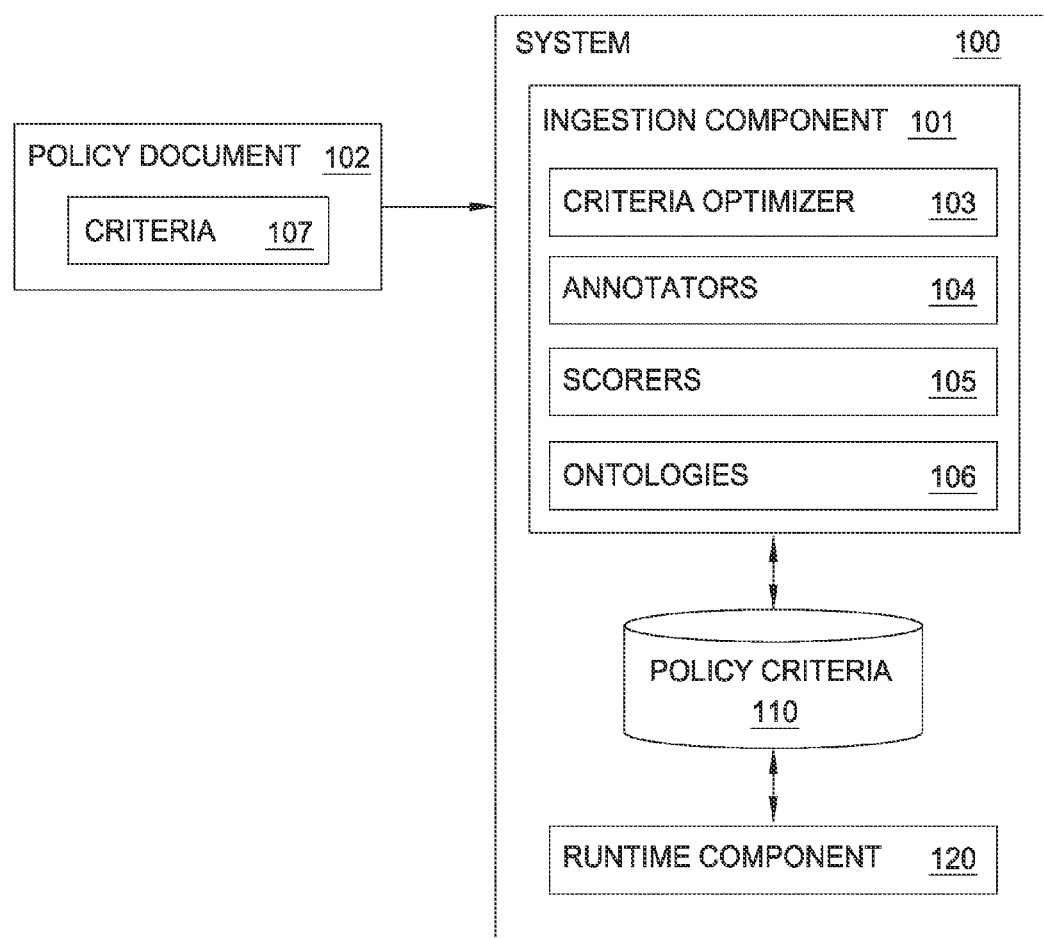
FIG. 1 illustrates a logical view of a system configured to perform criteria modification to improve analysis, according to one embodiment.

Embodiments disclosed herein provide techniques to intelligently modify policy criteria to improve system analysis. Generally, embodiments disclosed herein leverage anaphora and concept associations to determine whether to split a single criterion into multiple criteria or join multiple criteria into a single criterion. Anaphora is the repetition of a word (or group of words), or a synonym (or substitute) for a preceding word (or group of words). Written works often use anaphoric words among multiple statements to create relationships between the statements. Concepts may generally be defined as a type or generalized type of thing. Examples of concepts include, without limitation, age, primary diagnosis, and medications.

For example, a policy document may specify criteria that are used to determine whether a patient can join a medical study or receive a particular treatment. The policy document may include the following text:

1) Fasting cholesterol<=300 mg/dL and triglycerides<=2.5 times I ULN; 2) patients may be on lipid-lowering agents to reach these values.

By including the semicolon and/or numerals, the text appears to indicate that there are two distinct criteria. Traditional ingestion techniques may indeed consider these criteria as two separate criteria. However, embodiments disclosed herein may identify the anaphora of "these values" which refers back to "cholesterol" and "triglyceride" levels, and combine these criteria into a single criterion.

As another example, the policy document may include the following text:

Patients must not have an organ allograft or other history of immune compromise; patients must not be receiving chronic, systemic treatment with corticosteroids or other immunosuppressive agents.

This portion of text does not include anaphora or related concepts. Therefore, embodiments disclosed herein would separate these criteria into distinct criteria, whereas traditional techniques may consider them as a single criterion.

As used herein, a "policy document" includes any document which specifies criteria. The use of a specific type of policy document as a reference example herein should not be considered limiting of the disclosure. Examples of policy documents include, without limitation, medical studies, clinical trials, insurance policies, federal regulations, laws, and the like. For example, a policy document for a health insurance policy may include criteria used to determine whether the insurance policy covers a particular medical treatment. As another example, a policy document for a clinical trial may specify criteria used to determine whether a patient can participate in the clinical trial.

As previously indicated, several problems arise when policy documents contain individual criteria in unstructured form. For example, separate criteria may be tightly related, and should be combined into one criterion for processing. Similarly, a single delimited paragraph (or list item) may contain more criteria that can be properly be evaluated as an aggregate, and should be split into individual criteria. The way criteria are broken up or kept together can be detrimental to processing time and accuracy of evaluation and scoring. For example, processing A and B and C (where A, B, and C are individual criteria) has different characteristics than processing (A and B) and C. There is a grouping of A, B, and C which provides optimal processing even though any grouping gives the same result. Advantageously, embodiments disclosed herein leverage anaphora and concepts to determine optimal groupings of criteria, improving processing time and accuracy of evaluation and scoring.

FIG. 1 illustrates a logical view of a system 100 configured to perform criteria modification to improve analysis, according to one embodiment. As shown, the system 100 includes an ingestion component 101, policy criteria 110, and a runtime component 120. The ingestion component 101 is configured to extract criteria 107 from policy document 102. The ingestion component may then store the extracted criteria 107 in the policy criteria 110. The runtime component 120 may then determine whether a case submitted by a user satisfies the policy document 102 by referencing the stored policy criteria 110. A "case," as used herein, refers to a collection of data attributes submitted for analysis. Stated differently, a case may be considered a question and a set of supporting data. Examples of questions in a case may be "does this patient meet the criteria of this clinical trial," or "does the insurance policy require payment for an incident based on guideline X." Examples of supporting data of a case include a patient's medical records, which specifies detailed information about the patient (such as age, gender, weight, history of disease, and the like), or a report describing the incident submitted under the insurance policy.

For example, the policy document 102 may specify criteria 107 for determining whether a patient can take a certain medication. The ingestion component 101 may extract the criteria 107 and store the criteria in the policy criteria 110. In at least one embodiment, the criteria in the policy criteria 110 are stored as Unstructured Information Management Architecture (UIMA) Common Analysis System (CAS) objects. The runtime component 120 may then receive a case which specifies attributes for a patient. The runtime component 120 may process the case to determine whether the patient's attributes satisfy the policy criteria 110. If the runtime component 120 determines that the patient's attributes satisfy the policy criteria 110, the patient may be eligible to take the medication. However, if the patient's attributes do not satisfy the policy criteria 110, the patient may not be eligible to take the medication. One example of a system including an ingestion component 101 and a runtime component 120 is Watson by the IBM Corporation of Armonk, N.Y.

As shown in FIG. 1, the ingestion component 101 includes a criteria optimizer 103, a set of annotators 104, a set of scorers 105, and one or more ontologies 106. The criteria optimizer 103 is configured to join or separate criteria 107 in a policy document using natural language processing (or parsing) that leverages anaphora and/or concepts in the policy document 102. For example, "cholesterol" may be a concept in a medical record, and "these values" may be an anaphora that refers back to the patient's cholesterol. More generally, the ingestion component 101 may initially determine individual criteria by considering the location of structural constructs (e.g., line breaks, indentation, header information), symbolic characters (e.g., bullets such as hyphens or asterisks), or the presence of list prefix delimiters (e.g., ordered list numbers, letters, Roman numerals, or predefined labels).

The criteria optimizer 103 may further determine to leave some criteria unmodified. Generally, the criteria optimizer 103 is configured to process each criterion 107 in the policy document by annotating concepts over each criterion 107 and annotating candidate anaphoric words over each criterion 107. The criteria optimizer 103 may then determine if a criterion 107 contains indications that it may be a candidate for splitting into separate criterion. The criteria optimizer 103 may identify candidates using natural language parsing, such as detecting semicolons, periods, tabs, returns, or other delimiters in text. For example, the criteria optimizer 103 may use natural language processing to identify the semicolon in the following text as a delimiter that separates two criteria: "primary tumor is unresectable; it must be stable or asymptomatic." The criteria optimizer 103 may then split criteria 107 into separate criteria, or combine separate criteria 107 into a single criterion. Generally, the criteria optimizer 103 splits criteria when anaphora are not present in the criteria or a similarity score computed for two concepts in the criteria does not exceed a similarity threshold (i.e., the concepts are not sufficiently similar). The criteria optimizer 103 may combine criteria with other criteria when the criteria include overlapping concepts or anaphoric words that establish an anaphoric relationship to other criteria.

The annotators 104 include analysis modules configured to extract structured information from unstructured data. Examples of annotators 104 include annotators configured to perform natural language processing, identify delimiters in text, identify criteria, identify anaphora, and identify concepts. The scorers 105 are generally configured to compute similarity scores for concepts based on the distance between concepts in the ontologies 106. The ontologies 106 provide a structural framework for organizing information. An ontology formally represents knowledge as a set of concepts within a domain, and the relationships between those concepts.

Figure 2:
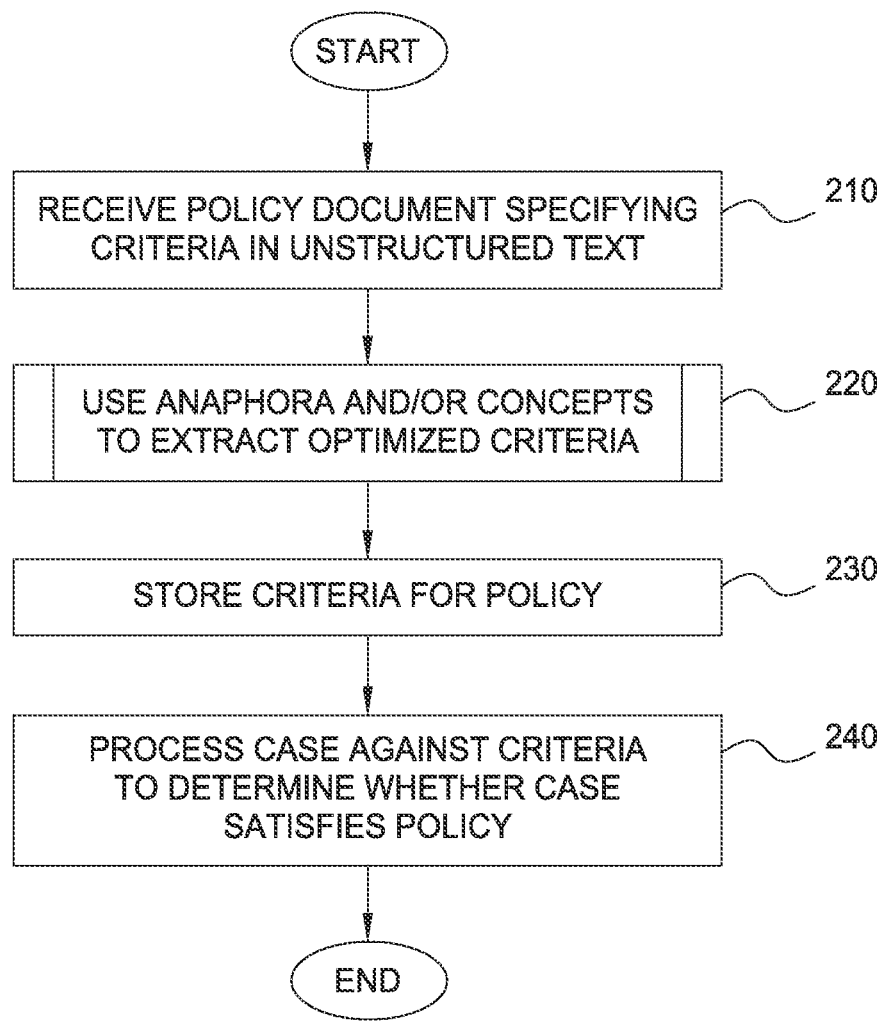
FIG. 2 is a flow chart illustrating a method for criteria modification to improve analysis, according to one embodiment.

FIG. 2 is a flow chart illustrating a method 200 for criteria modification to improve analysis, according to one embodiment. The steps of the method 200 provide enhanced techniques to extract criteria from a policy document to improve ingestion processing time, improve runtime processing time, and the accuracy of evaluation and/or scoring of criteria. As shown, the method 200 begins at step 210, where the ingestion component 101 receives a policy document which includes criteria in the form of unstructured text. At step 220, described in greater detail in FIG. 3, the criteria optimizer 103 may use anaphora and/or concepts in the policy document to extract optimized criteria from the policy document. Generally, the criteria optimizer 103 may identify criteria in the text of the policy document, and determine to join related criteria, break up a single criterion into multiple criteria, or determine to leave certain criteria unmodified. For example, the policy document may include the following text: "Primary tumor is unresectable; it must be stable or asymptomatic." The criteria optimizer 103 may identify the anaphora "it" in the text, and determine that the text only includes a single criterion. In such a scenario, if the text was considered to include multiple criteria, the criteria optimizer 103 would join the criteria into a single criterion. However, if the text was considered to include a single criterion, the criteria optimizer 103 would not modify the status of being a single criterion.

At step 230, the criteria optimizer 103 and/or the ingestion component 101 may store the extracted criteria in the policy criteria 110. At step 240, the runtime component 120 may receive a case from a user, and process the case against the criteria to determine whether the case satisfies the policy. Continuing with the tumor example, the runtime component 120 may determine whether the case (which may include a patient's detailed medical history) indicates that the patient's tumor is unresectable and stable or asymptomatic. The policy document may, for example, determine whether a patient can receive a treatment. If the patient's tumor satisfies all the criteria of the policy document, the runtime component 120 may return an indication that the patient can receive the treatment.

Figure 3:
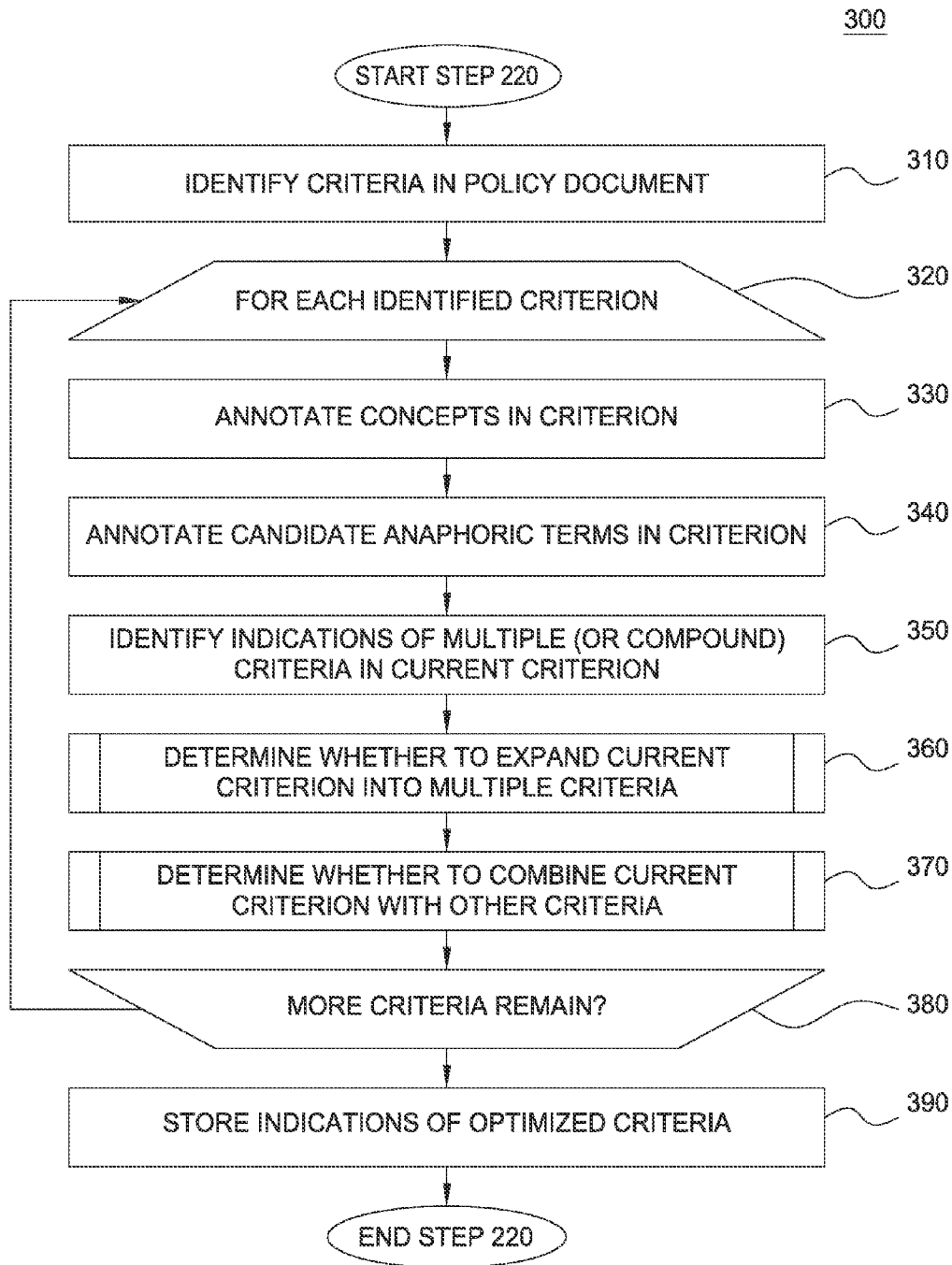
FIG. 3 is a flow chart illustrating a method to use anaphora to identify criteria, according to one embodiment.

FIG. 3 is a flow chart illustrating a method 300 corresponding to step 220 to use anaphora to identify criteria, according to one embodiment. In at least one embodiment, the criteria optimizer 103 performs the steps of the method 300. At step 310, the criteria optimizer 103 may parse the policy document to identify criteria in the document text. In at least one embodiment, the criteria optimizer 103 uses one or more annotators 104 to identify the criteria. In some embodiments, a set of criteria may be identified based on delimiters in the text, such as semicolons, line breaks, periods, and the like. At step 320, the criteria optimizer 103 executes a loop including steps 330-380 for each criterion identified at step 310. At step 330, the criteria optimizer 103 may invoke an annotator 104 to identify one or more concepts in each criterion. For example, in the text "patient has ECOG performance status of 0-2, patient's performance was determined within the previous 30 days" the annotator 104 may identify "ECOG performance status" as a concept. At step 340, the criteria optimizer 103 may invoke an annotator 104 to identify candidate anaphoric terms in the current criterion. Continuing with the previous example, the annotator 104 may identify "performance" as an anaphora for "ECOG performance status." At step 350, the criteria optimizer 103 may invoke an annotator 104 to identify indications of multiple (or compound) criteria in the current criterion. Examples of indications of multiple criteria include delimiters such as sentence boundaries (e.g., periods and semicolons), line breaks, or numbering (or other list formatting).

At step 360, described in greater detail with reference to FIG. 4, the criteria optimizer 103 determines whether to expand the current criterion into multiple criteria. Generally, the criteria optimizer 103 executes step 360 responsive to identifying indications of multiple (or composite) criteria at step 350. Once the indications are identified, the criteria optimizer 103 may break up the criteria according to the delimiters found in the text. At step 370, described in greater detail with reference to FIG. 5, the criteria optimizer 103 determines whether to combine the current criterion with other criteria. The criteria optimizer 103 may combine the current criterion with nearby criteria (in the text), or criteria from other locations in the text. At step 380, the criteria optimizer 103 determines whether more criteria remain in the policy text. If more criteria remain, the criteria optimizer 103 returns to step 320, otherwise the criteria optimizer 103 proceeds to step 390, where the criteria optimizer 103 stores indications of the optimized criteria.

Figure 4:
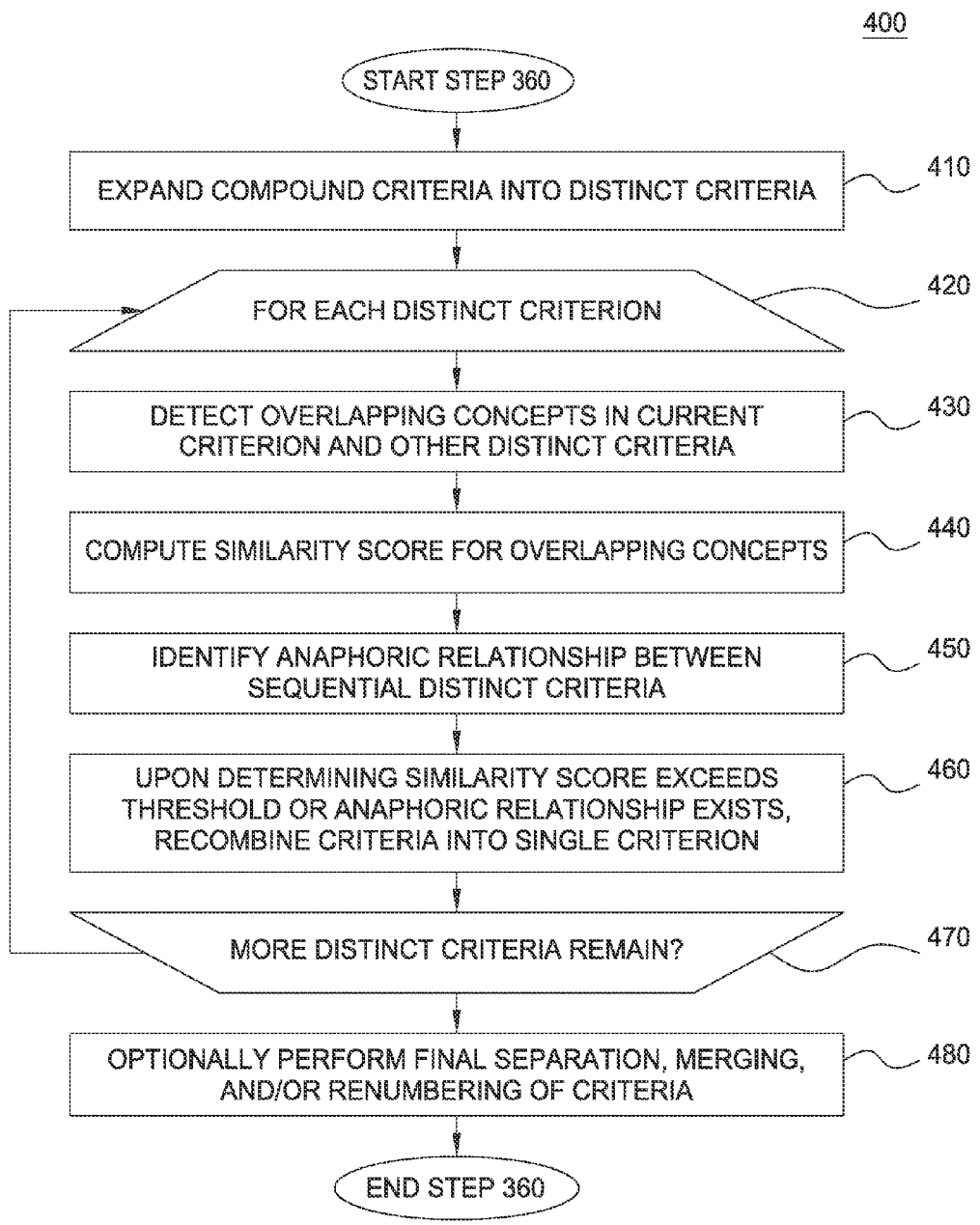
FIG. 4 is a flow chart illustrating a method to determine whether to expand a criterion into multiple criteria, according to one embodiment.

FIG. 4 is a flow chart illustrating a method 400 corresponding to step 360 to determine whether to expand a criterion into multiple criteria, according to one embodiment. In at least one embodiment, the criteria optimizer 103 performs the steps of the method 400. As shown, the method 400 begins at step 410, where the criteria optimizer 103 expands the compound criteria into multiple distinct criteria. In at least one embodiment, the criteria optimizer 103 may use the delimiters identified at step 350 to break up criteria. For example, if the text includes three sentences all ending in periods, the criteria optimizer 103 may identify the periods and break the text into three individual sentences, each of which is considered to have at least one respective distinct criterion. At step 420, the criteria optimizer 103 executes a loop including steps 430-470 for each distinct criterion created at step 410. At step 430, the criteria optimizer 103 may invoke an annotator 104 that identifies overlapping concepts (e.g., similar concepts which are present in the current criterion as well as other criteria in the policy). At step 440, the criteria optimizer 103 may invoke a scorer 105 to compute a similarity score for the overlapping concepts. In at least one embodiment, the similarity score may be computed based on a distance between the concepts in an ontology. Generally, the shorter the distance between the concepts in the ontology, the more likely the concepts are related, producing a higher similarity score. For example, the concepts "cancer" and "carcinoma" may be relatively close in an ontology, thereby reflecting a similarity between the concepts. Therefore, the criteria optimizer 103 and/or the scorer 105 may compute a high similarity score for the concepts. Conversely, the concepts "hamburger" and "earmuffs" are likely to be very distant in an ontology, reflecting a low degree of similarity. Therefore, a low similarity score may be computed for these concepts. Generally, the criteria optimizer 103 may compare the computed similarity score to a similarity threshold, and recombine (or keep intact) criteria having a similarity score that exceeds the threshold.

At step 450, the criteria optimizer 103 may invoke an annotator 104 to identify anaphoric relationships between the current criterion and an adjacent criterion (relative to their positions in the text). An example portion of policy text may read: "Patients with a current condition of osteopenia or osteoporosis via a Dual Energy X-ray Absorptiometry (DEXA) scan; patients with a history of either are allowed." The criteria optimizer 103 may have split the text into two criteria, namely "Patients with a current condition of osteopenia or osteoporosis via a Dual Energy X-ray Absorptiometry (DEXA) scan" and "patients with a history of either are allowed." At step 450, the criteria optimizer 103 may identify the term "either" when processing the second criterion, and determine that the term "either" is an anaphora for osteopenia and/or osteoporosis. Because of this relationship, the criteria optimizer 103 may determine to recombine these criteria into a single criterion. Therefore, at step 460, the criteria optimizer 103 may recombine the criteria into a single criterion upon determining the similarity score computed at step 440 exceeds a similarity threshold, or upon determining that the anaphoric relationship exists.

Figure 5:
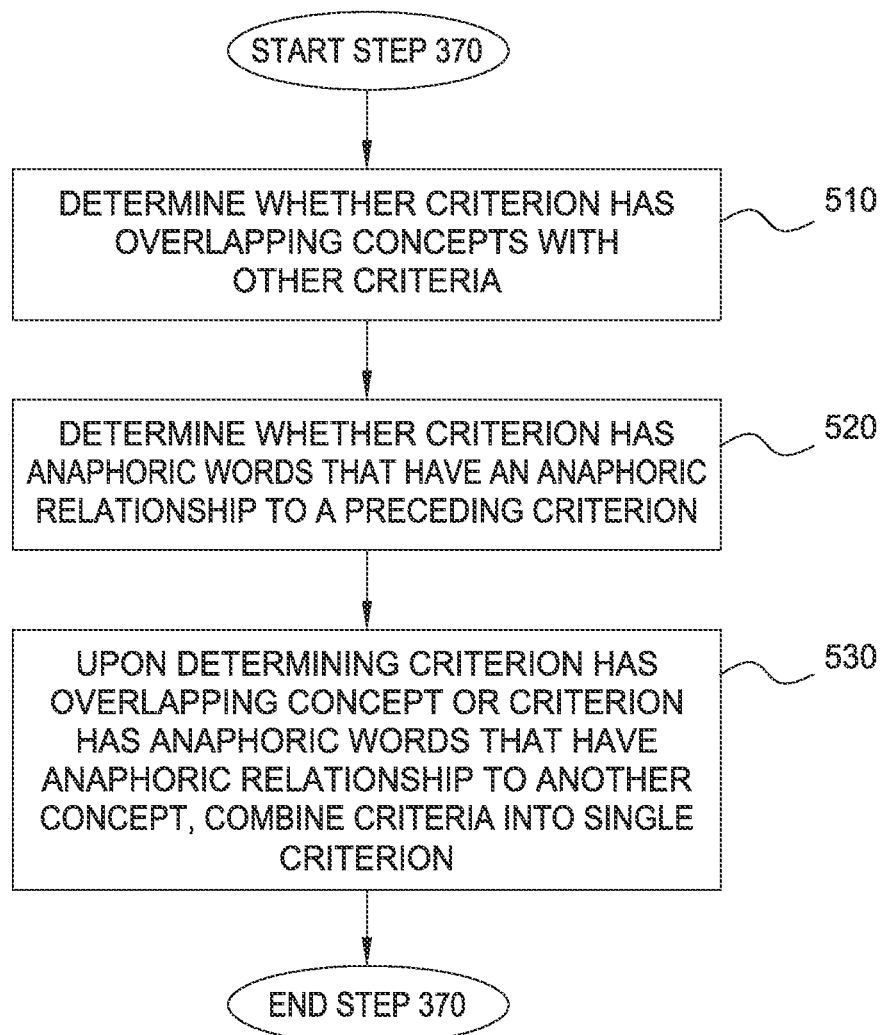
FIG. 5 is a flow chart illustrating a method to determine whether to combine a criterion with other criteria, according to one embodiment.

FIG. 5 is a flow chart illustrating a method 500 corresponding to step 370 to determine whether to combine a criterion with other criteria, according to one embodiment. In at least one embodiment, the criteria optimizer 103 performs the steps of the method 500. As shown, the method 500 begins at step 510, where the criteria optimizer 103 determines whether a criterion has overlapping concepts with other criteria. For example, the criteria optimizer 103 may invoke an annotator 104 to identify concepts in a criterion that are similar to other concepts in other criteria. In at least one embodiment, the criteria optimizer 103 computes a score for the overlapping concepts based on distance between the concepts in an ontology. At step 520, the criteria optimizer 103 may determine whether the current criterion has anaphoric words that have an anaphoric relationship to a preceding (or subsequent) criterion. For example, the following two criteria may be in the policy text: "patient has cholesterol>=200" and "it was taken within the previous 30 days." By identifying the anaphora "it," the criteria optimizer 103 may determine an anaphoric relationship exists between the two criteria, and combine the criteria into a single criterion. At step 530, the criteria optimizer 103 combines criteria that have overlapping concepts and/or have anaphoric relationships. In at least one embodiment, the criteria optimizer 103 determines that the concepts are "overlapping" upon determining that the similarity score for the concepts exceeds a similarity threshold. The criteria optimizer 103 may combine the criteria upon determining the concepts are overlapping based on the similarity score exceeding the threshold.

Figure 6:
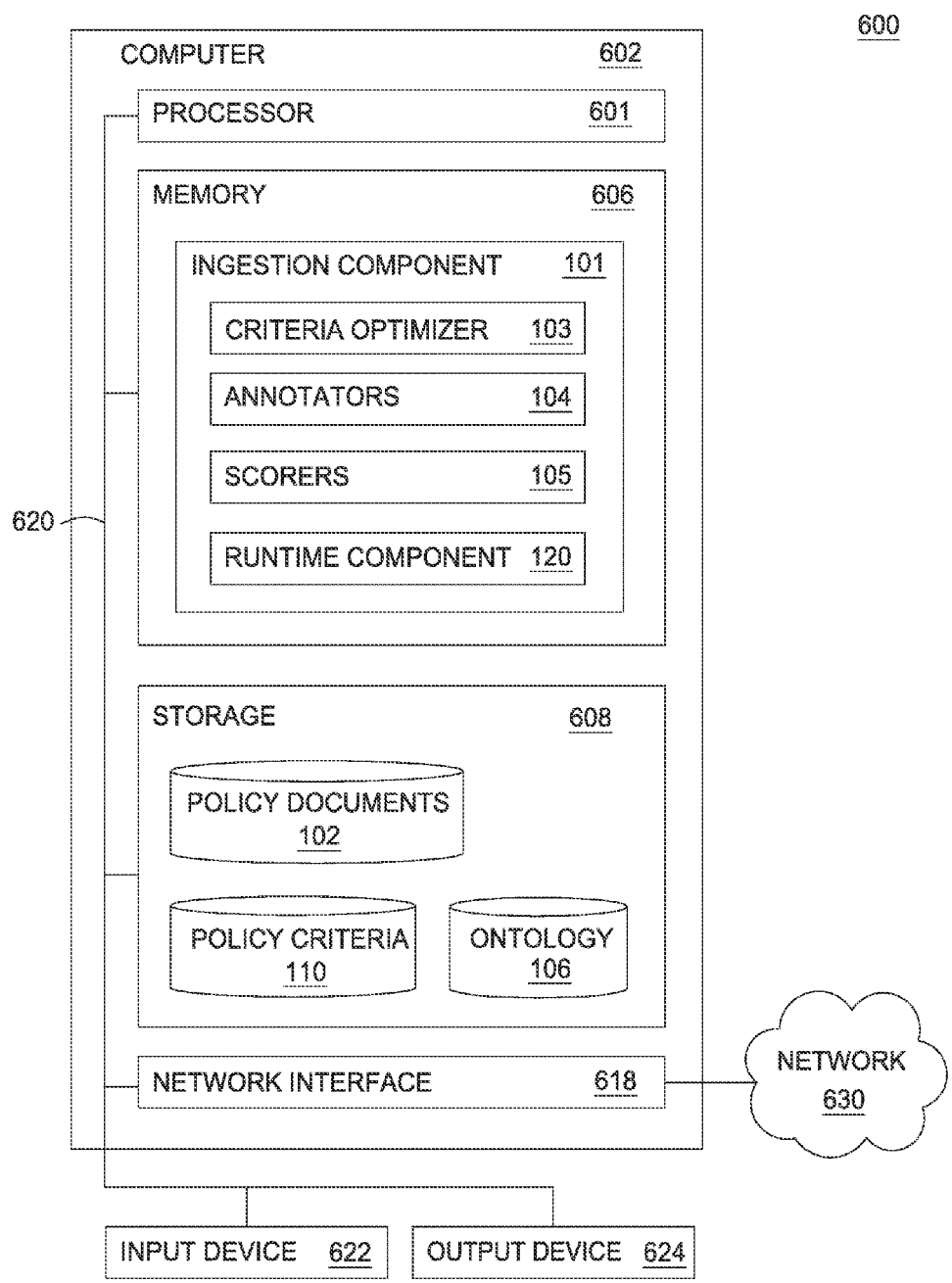
FIG. 6 is a block diagram illustrating a system which performs criteria modification to improve analysis, according to one embodiment.

FIG. 6 is a block diagram illustrating a system 600 which performs criteria modification to improve analysis, according to one embodiment. The networked system 600 includes a computer 602. The computer 602 may also be connected to other computers via a network 630. In general, the network 630 may be a telecommunications network and/or a wide area network (WAN). In a particular embodiment, the network 630 is the Internet.

The computer 602 generally includes a processor 604 which obtains instructions and data via a bus 620 from a memory 606 and/or a storage 608. The computer 602 may also include one or more network interface devices 618, input devices 622, and output devices 624 connected to the bus 620. The computer 602 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 604 is a programmable logic device that performs instruction, logic, and mathematical processing, and may be representative of one or more CPUs. The network interface device 618 may be any type of network communications device allowing the computer 602 to communicate with other computers via the network 630.

The storage 608 is representative of hard-disk drives, solid state drives, flash memory devices, optical media and the like. Generally, the storage 608 stores application programs and data for use by the computer 602. In addition, the memory 606 and the storage 608 may be considered to include memory physically located elsewhere; for example, on another computer coupled to the computer 602 via the bus 620.

The input device 622 may be any device for providing input to the computer 602. For example, a keyboard and/or a mouse may be used. The input device 622 represents a wide variety of input devices, including keyboards, mice, controllers, and so on. Furthermore, the input device 622 may include a set of buttons, switches or other physical device mechanisms for controlling the computer 602. The output device 624 may include output devices such as monitors, touch screen displays, and so on.

As shown, the memory 606 contains the ingestion component 101, which includes the criteria optimizer 103, annotators 104, and scorers 105. The memory 606 further includes the runtime component 120. As shown, the storage 608 contains data stores for policy documents 102, policy criteria 110, and one or more ontologies 106. Generally, the computer 602 implements all of the methods and functionality described with respect to FIGS. 1-5.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the foregoing, reference is made to embodiments presented in this disclosure. However, the scope of the present disclosure is not limited to specific described embodiments. Instead, any combination of the recited features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the recited aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system."

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the FIGS. illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the disclosure may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present disclosure, a user may access applications or related data available in the cloud. For example, the ingestion component 101 could execute on a computing system in the cloud and process policy documents. In such a case, the ingestion component could extract optimized policy criteria and store the extracted criteria at a storage location in the cloud. Doing so allows a user to access this information from any computing system attached to a network connected to the cloud (e.g., the Internet).

While the foregoing is directed to embodiments of the present disclosure, other and further embodiments of the disclosure may be devised without departing from the basic scope thereof, and the scope thereof is determined by the claims that follow.

What is claimed is:

1. A method comprising:
receiving an electronic policy document specifying a plurality of criteria;
identifying, in a segment of unstructured text in the policy document, a criteria delimiter;
identifying a first portion and a second portion of the segment of unstructured text, wherein the first and second portions are identified based on the criteria delimiter, wherein the first and second portions comprise a first criterion and a second criterion, respectively, wherein the first criterion comprises text in the policy document specifying: a first concept, a value for the first concept, and a first operator for the value for the first concept, wherein the second criterion comprises text in the policy document specifying: a second concept, a value for the second concept, and a second operator for the value for the second concept;

identifying, by a first annotator of a plurality of annotators, an anaphora in the second portion of the segment of unstructured text that relates the second concept to the first concept;

combining, based on the identified anaphora, the first criterion and the second criterion into a composite criterion, wherein the composite criterion comprises the first and second concepts, at least one of the first and second operators, and at least one of the values for the first and second concepts; and storing an indication that the composite criterion is one of the plurality of criteria for the policy document, wherein combining the first and second criteria reduces an amount of processing resources required to process cases against the plurality of criteria of the policy document relative to processing cases without combining the first and second criteria.

2. The method of claim 1, wherein the indication is stored as an Unstructured Information Management Architecture (UIMA) Common Analysis System (CAS) object, the method further comprising determining that the first and second criteria are related criteria by:

identifying the first concept in the first portion of the segment of unstructured text and the; second concept in the second portion of the segment of unstructured text;

determining a distance between a first concept node of an ontology and a second concept node of the ontology, wherein the first and second nodes of the ontology are related to the first and second concepts, respectively;

computing a score for the first concept and the second concept, wherein the similarity score is based on the distance between the first concept node and the second concept node in the ontology and reflects a level of similarity between the first and second concepts; and prior to combining the first criterion and the second criterion into the composite criterion, determining that the similarity score exceeds a similarity threshold.

3. The method of claim 2, wherein the segment of unstructured text comprises a single criterion prior to identifying the first and second portions of the unstructured text, the method further comprising:

upon determining that (i) the score does not exceed the similarity threshold, and (ii) the anaphora does not relate the second concept to the first concept:
refraining from combining the first and second criteria into a composite criteria; and
storing an indication that the first and second criteria are distinct criteria for the policy document.

4. The method of claim 1, wherein the composite criterion further comprises the first and second operators and the values for the first and second concepts.

5. The method of claim 1, further comprising:
receiving a first case comprising a plurality of attributes;
processing the plurality of attributes of the first case against the plurality of criteria of the policy document;
determining that the at least one of the first and second operators of the composite criterion applied to a first attribute value of a first attribute of the plurality of attributes does not satisfy the at least one of the values for the first and second concepts of the composite criterion; and determining that the first case does not satisfy the criteria of the policy document.

6. The method of claim 1, further comprising:
identifying, by a second annotator of the plurality of annotators, a plurality of concepts including the first and second concepts in the policy document, wherein the anaphora further relates the value for the second concept to the value for the first concept, wherein the plurality of annotators comprise: (i) natural language processors, (ii) annotators configured to identify delimiters in electronic text, (iii) annotators configured to identify one or more criteria, (iv) annotators configured to identify anaphora, and (v) annotators configured to identify one or more concepts.

7. The method of claim 1, wherein the criteria delimiter comprises one of: (i) a period, (ii) a semicolon, (iii) a comma, (iv) a line break, (v) a character, and (vi) a list prefix delimiter.

8. A system, comprising:
a processor; and
a memory containing a program which when executed by the processor performs an operation comprising:
receiving an electronic policy document specifying a plurality of criteria;
identifying, in a segment of unstructured text in the policy document, a criteria delimiter;
identifying a first portion and a second portion of the segment of unstructured text, wherein the first and second portions are identified based on the criteria delimiter, wherein the first and second portions comprise a first criterion and a second criterion, respectively, wherein the first criterion comprises text in the policy document specifying: a first concept, a value for the first concept, and a first operator for the value for the first concept, wherein the second criterion comprises text in the policy document specifying: a second concept, a value for the second concept, and a second operator for the value for the second concept;
identifying, by a first annotator of a plurality of annotators, an anaphora in the second portion of the segment of unstructured text that relates the second concept to the first concept;
combining, based on the identified anaphora, the first criterion and the second criterion into a composite criterion, wherein the composite criterion comprises the first and second concepts, at least one of the first and second operators, and at least one of the values for the first and second concepts; and
storing an indication that the composite criterion is one of the plurality of criteria for the policy document, wherein combining the first and second criteria reduces an amount of processing resources required to process cases against the plurality of criteria of the policy document relative to processing cases without combining the first and second criteria.

9. The system of claim 8, wherein the indication is stored as an Unstructured Information Management Architecture (UIMA) Common Analysis System (CAS) object, the operation further comprising determining that the first and second criteria are related criteria by:

identifying the first concept in the first portion of the segment of unstructured text and the; second concept in the second portion of the segment of unstructured text;

determining a distance between a first concept node of an ontology and a second concept node of the ontology, wherein the first and second nodes of the ontology are related to the first and second concepts, respectively;

computing a score for the first concept and the second concept, wherein the similarity score is based on the distance between the first concept node and the second concept node in the ontology and reflects a level of similarity between the first and second concepts; and prior to combining the first criterion and the second criterion into the composite criterion, determining that the similarity score exceeds a similarity threshold.

10. The system of claim 9, wherein the segment of unstructured text comprises a single criterion prior to identifying the first and second portions of the unstructured text, the operation further comprising:

upon determining that (i) the score does not exceed the similarity threshold, and (ii) the anaphora does not relate the second concept to the first concept:
refraining from combining the first and second criteria into a composite criteria; and
storing an indication that the first and second criteria are distinct criteria for the policy document.

11. The system of claim 8, wherein the composite criterion further comprises the first and second operators and the values for the first and second concepts.

12. The system of claim 8, the operation further comprising:

receiving a first case comprising a plurality of attributes;
processing the plurality of attributes of the first case against the plurality of criteria of the policy document;
determining that the at least one of the first and second operators of the composite criterion applied to a first attribute value of a first attribute of the plurality of attributes does not satisfy the at least one of the values for the first and second concepts of the composite criterion; and
determining that the first case does not satisfy the criteria of the policy document.

13. The system of claim 8, the operation further comprising:

identifying, by a second annotator of the plurality of annotators, a plurality of concepts including the first and second concepts in the policy document, wherein the anaphora further relates the value for the second concept to the value for the first concept, wherein the plurality of annotators comprise: (i) natural language processors, (ii) annotators configured to identify delimiters in electronic text, (iii) annotators configured to identify one or more criteria, (iv) annotators configured to identify anaphora, and (v) annotators configured to identify one or more concepts.

14. The system of claim 8, wherein the criteria delimiter comprises one of: (i) a period, (ii) a semicolon, (iii) a comma, (iv) a line break, (v) a character, and (vi) a list prefix delimiter.

15. A computer program product, comprising:
a computer-readable storage medium having computer-readable program code embodied therewith, the computer-readable program code executable by one or more computer processors to perform an operation comprising:
receiving an electronic policy document specifying a plurality of criteria;
identifying, in a segment of unstructured text in the policy document, a criteria delimiter;
identifying a first portion and a second portion of the segment of unstructured text, wherein the first and second portions are identified based on the criteria delimiter, wherein the first and second portions comprise a first criterion and a second criterion, respectively, wherein the first criterion comprises text in the policy document specifying: a first concept, a value for the first concept, and a first operator for the value for the first concept, wherein the second criterion comprises text in the policy document specifying: a second concept, a value for the second concept, and a second operator for the value for the second concept;
identifying, by a first annotator of a plurality of annotators, an anaphora in the second portion of the segment of unstructured text that relates the second concept to the first concept;
combining, based on the identified anaphora, the first criterion and the second criterion into a composite criterion, wherein the composite criterion comprises the first and second concepts, at least one of the first and second operators, and at least one of the values for the first and second concepts; and
storing an indication that the composite criterion is one of the plurality of criteria for the policy document, wherein combining the first and second criteria reduces an amount of processing resources required to process cases against the plurality of criteria of the policy document relative to processing cases without combining the first and second criteria.

16. The computer program product of claim 15, wherein the indication is stored as an Unstructured Information Management Architecture (UIMA) Common Analysis System (CAS) object, the operation further comprising determining that the first and second criteria are related criteria by:

identifying a first concept in the first portion of the segment of unstructured text and a second concept in the second portion of the segment of unstructured text;
determining a distance between a first concept node of an ontology and a second concept node of the ontology, wherein the first and second nodes of the ontology are related to the first and second concepts, respectively;
computing a score for the first concept and the second concept, wherein the similarity score is based on the distance between the first concept node and the second concept node in the ontology and reflects a level of similarity between the first and second concepts; and
prior to combining the first criterion and the second criterion into the composite criterion, determining that the similarity score exceeds a similarity threshold.

17. The computer program product of claim 16, wherein the segment of unstructured text comprises a single criterion prior to identifying the first and second portions of the unstructured text, the operation further comprising:

upon determining that (i) the score does not exceed the similarity threshold, and (ii) the anaphora does not relate the second concept to the first concept:
refraining from combining the first and second criteria into a composite criteria; and
storing an indication that the first and second criteria are distinct criteria for the policy document.

18. The computer program product of claim 15, wherein the composite criterion further comprises the first and second operators and the values for the first and second concepts.

19. The computer program product of claim 15, wherein the criteria delimiter comprises one of: (i) a period, (ii) a semicolon, (iii) a comma, (iv) a line break, (v) a character, and (vi) a list prefix delimiter, the operation further comprising:

receiving a first case comprising a plurality of attributes;

processing the plurality of attributes of the first case against the plurality of criteria of the policy document;

determining that the at least one of the first and second operators of the composite criterion applied to a first attribute value of a first attribute of the plurality of attributes does not satisfy the at least one of the values for the first and second concepts of the composite criterion; and determining that the first case does not satisfy the criteria of the policy document.

20. The computer program product of claim 15, the operation further comprising:

identifying, by a second annotator of the plurality of annotators, a plurality of concepts including the first and second concepts in the policy document, wherein the anaphora further relates the value for the second concept to the value for the first concept, wherein the plurality of annotators comprise: (i) natural language processors, (ii) annotators configured to identify delimiters in electronic text, (iii) annotators configured to identify one or more criteria, (iv) annotators configured to identify anaphora, and (v) annotators configured to identify one or more concepts.

* * * * *